United States Patent
Collins

(10) Patent No.: US 9,889,030 B2
(45) Date of Patent: Feb. 13, 2018

(54) ENDOGRAFT DELIVERY DEVICE ASSEMBLY

(71) Applicant: Cook Medical Technologies LLC, Bloomington, IN (US)

(72) Inventor: James Collins, Paddington (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 15/203,095

(22) Filed: Jul. 6, 2016

(65) Prior Publication Data

US 2017/0049595 A1 Feb. 23, 2017

(30) Foreign Application Priority Data

Aug. 20, 2015 (AU) .............................. 2015215913

(51) Int. Cl.
*A61F 2/966* (2013.01)
*A61F 2/07* (2013.01)

(52) U.S. Cl.
CPC ............... *A61F 2/966* (2013.01); *A61F 2/07* (2013.01)

(58) Field of Classification Search
CPC .. A61F 2/95; A61F 2/962; A61F 2/966; A61F 2/9665; A61F 2002/9511; A61F 2002/823; A61F 2/07; A61F 2002/9517; A61M 25/104; A61M 25/0026
See application file for complete search history.

(56) References Cited

U.S. PATENT DOCUMENTS

2004/0010265 A1* 1/2004 Karpiel ..................... A61F 2/95
606/108
2010/0030255 A1* 2/2010 Berra ........................ A61F 2/07
606/200
(Continued)

FOREIGN PATENT DOCUMENTS

EP 2517671 A2 10/2012
EP 2724694 A2 4/2014
(Continued)

OTHER PUBLICATIONS

Extended European Search Report, Cook Medical Technologies LLC, dated Oct. 6, 2016.

*Primary Examiner* — Eric Rosen
*Assistant Examiner* — Mikail Mannan
(74) *Attorney, Agent, or Firm* — Richard J. Godlewski

(57) ABSTRACT

An endograft delivery device assembly is disclosed. The assembly comprises: a tip; a guide wire cannula, the guide wire cannula; a pusher disposed around the guide wire cannula, the pusher having a sheath assembly receiving portion at a proximal end thereof and a main portion extending distally from the sheath assembly receiving portion to a distal end, the sheath assembly receiving portion having at least one longitudinally extending groove; and a sheath assembly slidably mounted to the sheath assembly receiving portion of the pusher. The sheath assembly has a sheath portion, mountable over a endograft, and slide connecter portion. The slide connector portion has at least one inwardly projecting key, the key keying with the groove. The sheath assembly is slidably movable from an extended position over the endograft to a retracted position in which the endograft is uncovered.

17 Claims, 10 Drawing Sheets

(56) References Cited

U.S. PATENT DOCUMENTS

| | | | | |
|---|---|---|---|---|
| 2010/0198328 A1* | 8/2010 | Hartley | ............ | A61F 2/95 623/1.11 |
| 2011/0015716 A1* | 1/2011 | Silverman | ............ | A61F 2/88 623/1.2 |
| 2011/0301685 A1* | 12/2011 | Kao | ............ | A61F 2/95 623/1.11 |
| 2013/0046373 A1 | 2/2013 | Cartledge et al. | | |

FOREIGN PATENT DOCUMENTS

| | | |
|---|---|---|
| EP | 2522315 B1 | 5/2014 |
| EP | 2724694 A3 | 1/2015 |
| EP | 2522316 B1 | 4/2015 |
| WO | 2007092276 A3 | 8/2007 |
| WO | 2008042266 A3 | 4/2008 |
| WO | 2010005524 A3 | 1/2010 |
| WO | 2010088027 A1 | 8/2010 |
| WO | 2011008538 A1 | 1/2011 |
| WO | 2011116308 A1 | 9/2011 |
| WO | 2014026173 A9 | 2/2014 |

\* cited by examiner

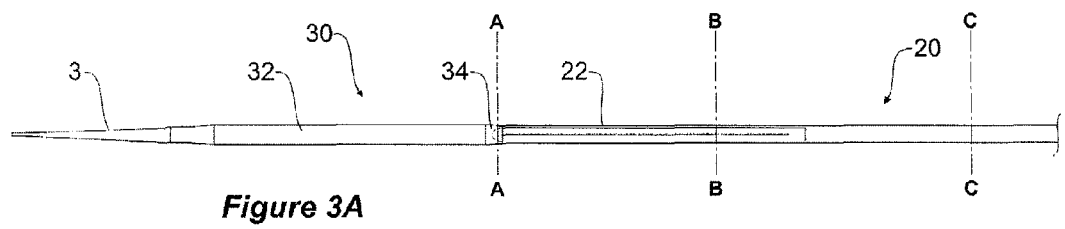
*Figure 3A*
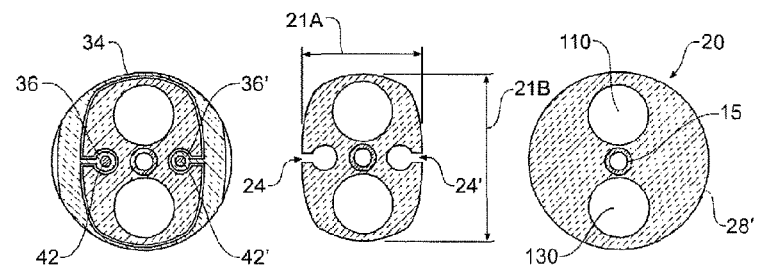
*Figure 4*  *Figure 5A*  *Figure 6*
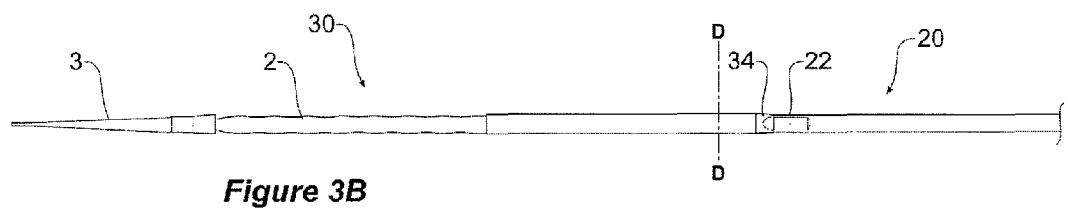
*Figure 3B*

ENDOGRAFT DELIVERY DEVICE ASSEMBLY

CROSS REFERENCE TO RELATED APPLICATIONS

This application claims the benefit of Australian patent application 2015215913 filed on Aug. 20, 2015 entitled AN ENDOGRAFT DELIVERY DEVICE ASSEMBLY the entire contents of which are incorporated herein by reference.

FIELD OF THE INVENTION

The present invention relates to endografts and their delivery systems. In particular, the present invention related to delivery device assemblies capable of delivering stent grafts into the vascular system.

BACKGROUND OF THE INVENTION

Stent graft and delivery device assemblies are used in aortic intervention. They are used by vascular surgeons to treat aneurysms and to repair regions of the aorta, including the aortic arch, the thoracic aorta, the abdominal aorta and the aortic bifurcation. Current devices require, and include, a haemostatic valve so as to allow relative axial movement of components, while at the same time, minimising blood flow.

It is an object of the invention to provide an improved endograft and delivery device assembly that eliminates the need for a haemostatic valve and/or provides a simpler assembly.

Throughout this specification, the term "distal" with respect to a portion of the aorta, a deployment device or an endograft means the end of the aorta, deployment device or endograft further away in the direction of blood flow from the heart and the term "proximal" means the portion of the aorta deployment device or end of the endograft nearer to the heart in the direction of blood flow. When applied to other vessels, similar terms such as caudal and cranial should be understood.

SUMMARY OF THE INVENTION

According to a first aspect of the invention an endograft delivery device assembly is provided, the assembly comprising:
  a tip;
  a guide wire cannula, the guide wire cannula extending distally from the tip to a handle at a distal end of the delivery device assembly, the guide wire cannula slidable over a guide wire;
  a pusher disposed around the guide wire cannula, the pusher having a sheath assembly receiving portion at a proximal end thereof and a main portion extending distally from the sheath assembly receiving portion to a distal end, the sheath assembly receiving portion having at least one longitudinally extending groove; and
  a sheath assembly slidably mounted to the sheath assembly receiving portion of the pusher, the sheath assembly having a sheath portion, mountable over a endograft, and slide connecter portion, the slide connector portion having at least one inwardly projecting key, the key keying with the groove.

In one form the sheath assembly is slidably movable from an extended position over the endograft to a retracted position in which the endograft is uncovered.

In one form the assembly further comprises a sheath retraction assembly extending longitudinally through the pusher, the sheath retraction assembly connected to the key and actuatable so as to pull the sheath assembly from the extended position to the retracted position.

In one form the sheath retraction assembly comprises at least one sheath line, the at least one sheath line connected to the at least one key.

In one form the pusher includes a pair of longitudinally extending grooves and the slide connector portion includes a pair of inwardly projecting keys, the keys keying with the grooves.

In one form each groove comprises a slot opening into a line receiving passage.

In one form the sheath lines and the slots are mutually sized such that the sheath lines are captive within their respective line receiving passages.

In one form the sheath retraction assembly comprises a pair of sheath lines, each sheath line connected to a respective key.

In one form the pair of sheath lines are joined at a position distal of the keys and wherein a common sheath line extends distally to a pullable end, the pullable end adjacent to the handle.

In one form the sheath portion is tubular with a circular cross-section and wherein the sheath assembly receiving portion of the pusher has a major diameter and a minor diameter, the minor diameter less that the major diameter such that a void is formed between the sheath portion and the pusher when the pusher is in the retracted position.

In one form the groove(s) do not extent into the main portion of the sheath such that an outer surface of the main portion is smoother than the sheath assembly receiving portion.

In one form the outer surface of the main portion is substantially circular in cross-section.

In one form the pusher comprises a guide wire cannula receiving lumen and a pair of auxiliary lumens disposed either side of the guide wire cannula receiving lumen.

In one form the auxiliary lumens are pre-loaded with respective auxiliary guide wires.

In one form the endograft is a stent graft.

In one form the slide connecter portion transitions from a circular end to a non-circular end, the non-circular end shaped to follow an external shape of the sheath assembly receiving portion of the pusher.

In one form the sheath assembly comprises an endograft disposed between the guide wire cannula and the sheath portion of the sheath assembly.

In one form the endograft is a stent graft.

According to a second aspect of the invention an endograft and delivery device assembly is provided, the assembly comprising:
  a tip including a dilator portion;
  a guide wire cannula, the guide wire cannula extending distally from the tip to a handle at a distal end of the delivery device assembly, the guide wire cannula slidable over a guide wire;
  a pusher disposed around the guide wire cannula, the pusher having a sheath assembly receiving portion at a proximal end thereof and a main portion extending distally from the sheath assembly receiving portion to a distal end, the sheath assembly receiving portion having a pair of longitudinally extending grooves, each groove comprising a slot opening into a line receiving passage;

a sheath assembly slidably mounted to the sheath assembly receiving portion of the pusher, the sheath assembly having a sheath portion, mountable over a endograft, and slide connecter portion, the slide connector portion having a pair of inwardly projecting keys, the keys keying with the grooves; and a sheath retraction assembly extending longitudinally through the pusher, the sheath retraction assembly comprising a pair of sheath lines, each sheath line connected to a respective key, wherein the sheath retraction assembly is actuatable so as to pull the sheath assembly from an extended position over the endograft to a retracted position in which the endograft is uncovered.

In one form the sheath assembly comprises a stent graft disposed between the guide wire cannula and the sheath portion of the sheath assembly.

BRIEF DESCRIPTION OF THE DRAWING

Embodiments of the present invention will be discussed with reference to the accompanying drawings wherein:

FIG. 3A is a cross-sectional view of the assembly of FIG. 1A;

FIG. 3B is a cross-sectional view of the assembly of FIGS. 1A and 1B, in the retracted position of FIG. 1B;

FIG. 4 is a cross-sectional view through section lines A-A indicated on FIG. 3A;

FIG. 5A is a cross-sectional view through section lines B-B indicated on FIG. 3A;

FIG. 6 is a cross-sectional view through section lines C-C indicated on FIG. 3A;

DETAILED DESCRIPTION

Figure 1A:
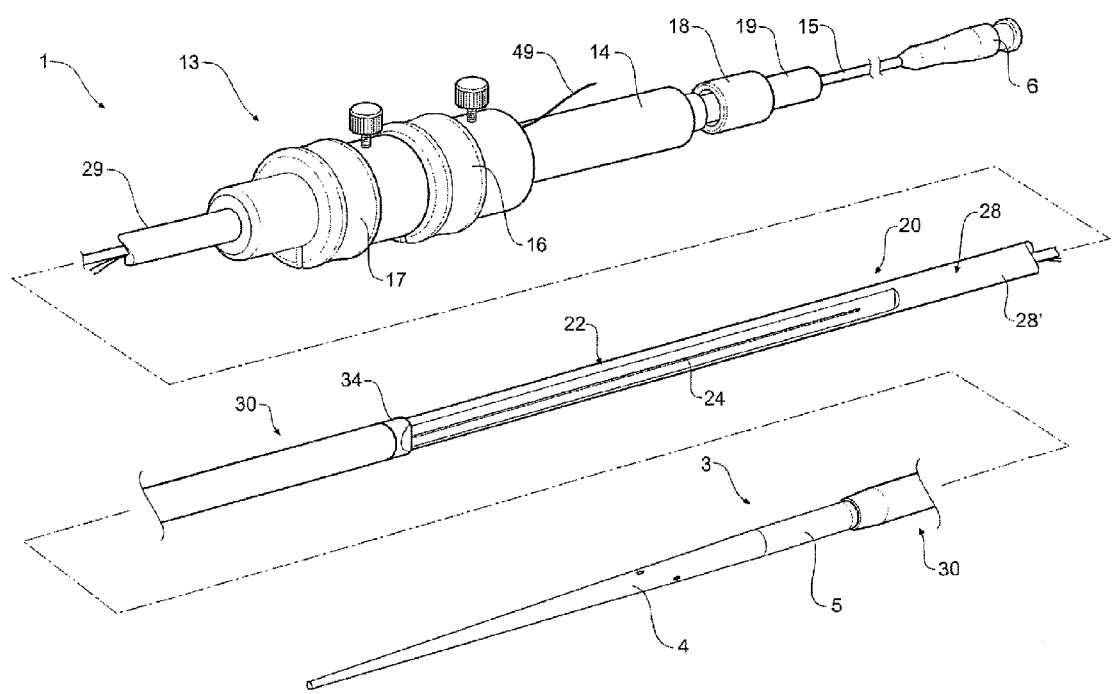
FIG. 1A shows a first embodiment of an endograft and delivery device assembly according to the invention in a diagrammatic isometric view with the endograft covered.
Figure 1B:
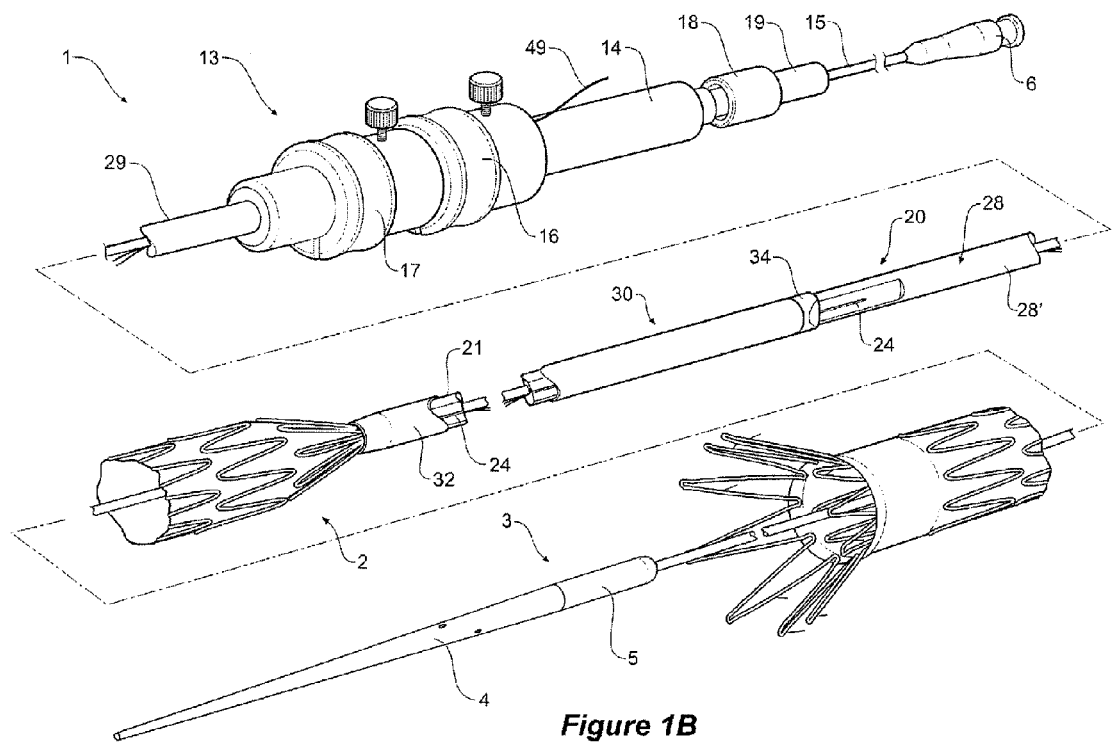
FIG. 1B is a similar view to that of FIG. 1A, but shows the endograft, in this case a stent graft, uncovered.
Figure 2:
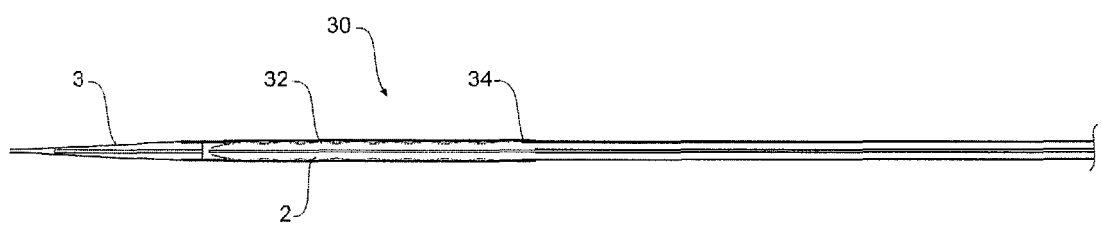
FIG. 2 is a side view of the assembly of FIG. 1A.

Referring to FIGS. 1A and 1B, an endograft delivery device assembly is shown. The assembly 1 comprises a tip 3, which, for this embodiment includes a dilator portion 4 at a proximal end thereof and a capsule assembly 5 at a distal end thereof. The assembly also comprises a guide wire cannula 15 that extends distally from the tip 3 to a handle 13 at a distal end of the delivery device. The guide wire cannula 15 is slidable over a guide wire, such as the guide wire 12 shown in FIG. 10A. A syringe connector 6 is shown at the distal end of the guide wire cannula 15. The assembly 1 also includes a pusher 20 disposed around the guide wire cannula 15, the pusher 20 having a sheath assembly receiving portion 22 at a proximal end 21 thereof and a main portion 28 extending distally from the sheath assembly receiving portion 22 to a distal end 29. The sheath assembly receiving portion 22 has at least one longitudinally extending groove 24, as can be seen in FIG. 1A.

The assembly also includes a sheath assembly 30 mounted to the sheath assembly receiving portion 22 of the pusher 20, as can be seen in FIGS. 1A, 1B, 2, 3A and 3B. The sheath assembly 30 has a sheath portion 32 and a slide connector portion 34, again shown in FIGS. 1A, 1B, 3A and 3B. The sheath portion 22 is mountable over an endograft, such as the stent graft 2 shown in FIGS. 1B and 3A.

The slide connector portion 34 of the sheath assembly 30 has at least one inwardly projecting key 36, as illustrated in the cross-sectional view of FIG. 4 taken through section lines A-A of FIG. 3A. The inwardly projecting key 36 keys with the longitudinally extending groove 24, as is most clearly shown in FIG. 8A.

The sheath assembly 30 is slidably movable from an extended position over the endograft, in this case stent graft 2, to a retracted position in which the endograft or stent graft 2 is uncovered. These two positions are shown in FIGS. 1A and 1B respectively.

Figure 8A:
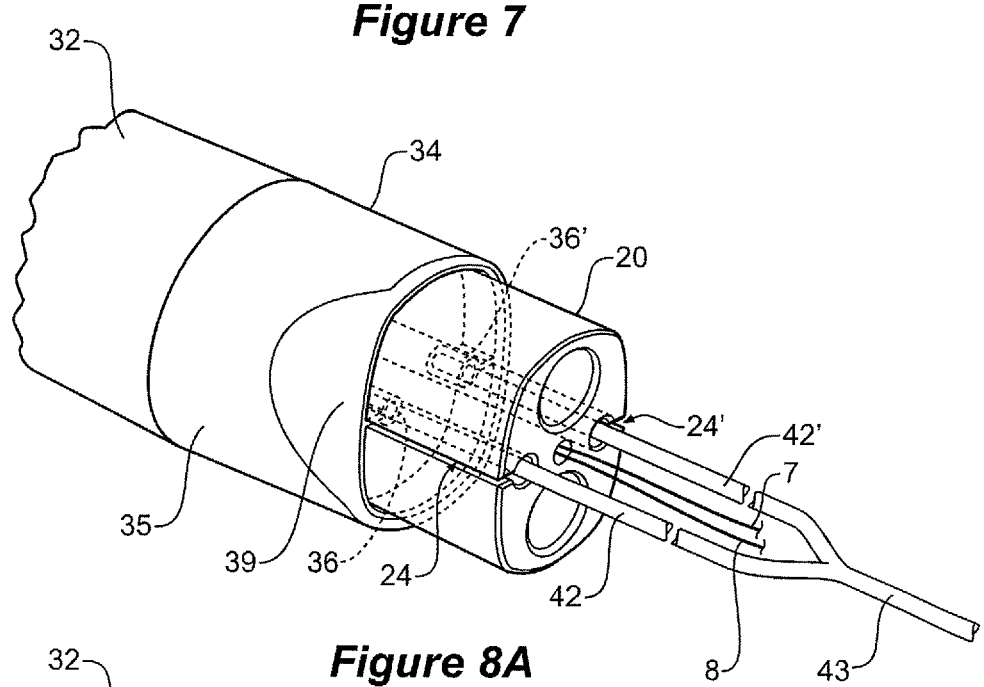
FIG. 8A is a detailed isometric view showing components of the endograft and delivery device assembly of FIG. 1, including a sheath assembly.

FIG. 8A shows that the slide connector portion 34 transitions from a circular end 35 to a non-circular end 39. The non-circular end 39 is shaped to follow an external shape of the sheath assembly receiving portion 22 of the pusher 20.

The sheath assembly 30 of the embodiment illustrated in FIGS. 3A and 3B for instance is constructed from two different materials. The sheath portion 32 is may be made from Nylon or another suitable flexible material. The slide connector portion 34 maybe Nylon 12, HDPP or another high strength material.

While in some embodiments of the invention a single inwardly projecting key may mate with a single groove, with the embodiment if the invention shown in the drawings and as described above, the pusher 20 includes a pair of longitudinally extending grooves 24 and 24' and a slide connector portion 34 includes a pair of inwardly projecting keys 36 and 36', the keys 36 and 36' keying with the grooves 24 and 24'. The slide connector portion 34 and its pair of inwardly projecting keys 36 and 36' can be seen in FIG. 4. The pair of longitudinally extending grooves 24 and 24' can be seen the cross-sectional views of FIGS. 5A and 5C, taken through section lines B-B on FIG. 3A. The slide connector portion 34 is also shown in an isometric view in FIG. 8A. This view shows more clearly how the inwardly projecting keys 36 and 36' slide within the pair of longitudinally extending grooves 24 and 24'.

The assembly 1 also includes a sheath retraction assembly extending longitudinally through the pusher 20. The sheath retraction assembly is connected to the key 36 or keys 36, 36' and is actuatable so as to pull the sheath assembly 30 from the extended position shown in FIG. 1A to the retracted position shown in FIG. 1B.

Figure 8B:
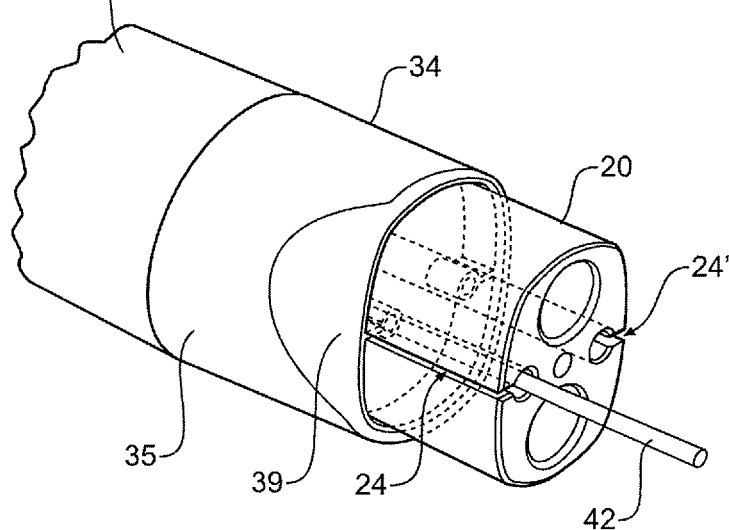
FIG. 8B is a similar view to FIG. 8A, but shows an alternative embodiment of the invention.

FIG. 8B shows an embodiment of the invention where a single sheath line 42 is provided. The sheath line 42 is connected to the key 36.

In the embodiment of the invention shown in FIG. 8A, a pair of sheath lines are provided, each sheath line 42, 42' connected to a respective key 36, 36'. The pair of sheath lines 42, 42' are joined at a position distal of the keys 36, 36' to a common sheath line 43 that extends distally to a pullable end 49, the pullable end 49 adjacent to the handle 13, having a handle body 14, as is shown in FIGS. 1A and 1B. A pin vice 18 having a screw cap 19 is provided for locking and unlocking the handle with respect to the guide wire 15.

The sheath lines 42, 42' and the common sheath line 43 are desirably constructed from a material that will not elongate to any significant extend during use. Engineering grade polymers such as Polypropylene or Nylon having that property may be used.

FIG. 8A also shows release wires 7, 8 that allow remote release of the proximal and distal ends of the stent graft 2 shown in FIG. 1B. Proximal and distal wire release mechanisms 16, 17 are also shown in FIGS. 1A and 1B.

Figure 5B:
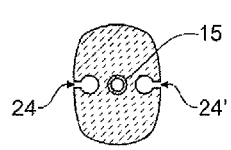
FIG. 5B is a cross-sectional view through section lines B-B of an alternative embodiment of the invention.
Figure 5C:
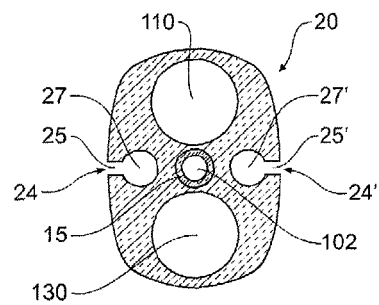
FIG. 5C is an enlarged version of FIG. 5A taken through indicated on FIG. 3A.

Referring now to FIG. 5C, an enlarged cross-sectional view through section lines B-B on FIG. 3A, it can be seen that the grooves 24, 24' each comprise a slot opening 25,25' opening into a line receiving passage 27,27'. The Sheath lines 42,42' and the slots 25,25' are mutually sized such that the sheath lines 42,42' are captive within their respective line receiving passages 27,27'.

FIG. 5B is a cross-sectional view through section lines B-B of an alternative embodiment of the invention to that shown in FIGS. 4, 5A and 6. With this embodiment, the pusher 20 accommodates a guide wire cannula 15 and includes grooves 24 and 24', but does not have auxiliary lumens.

In contrast to the embodiment of the invention shown in FIG. 5B, the embodiment of the invention shown in FIGS. 4, 5A and 6 includes auxiliary lumens as is illustrated most clearly in FIG. 5C. More specifically, the pusher 20 includes a pair of auxiliary lumens 110, 130 disposed either side of a guide wire cannula receiving lumen 102.

Figure 11:
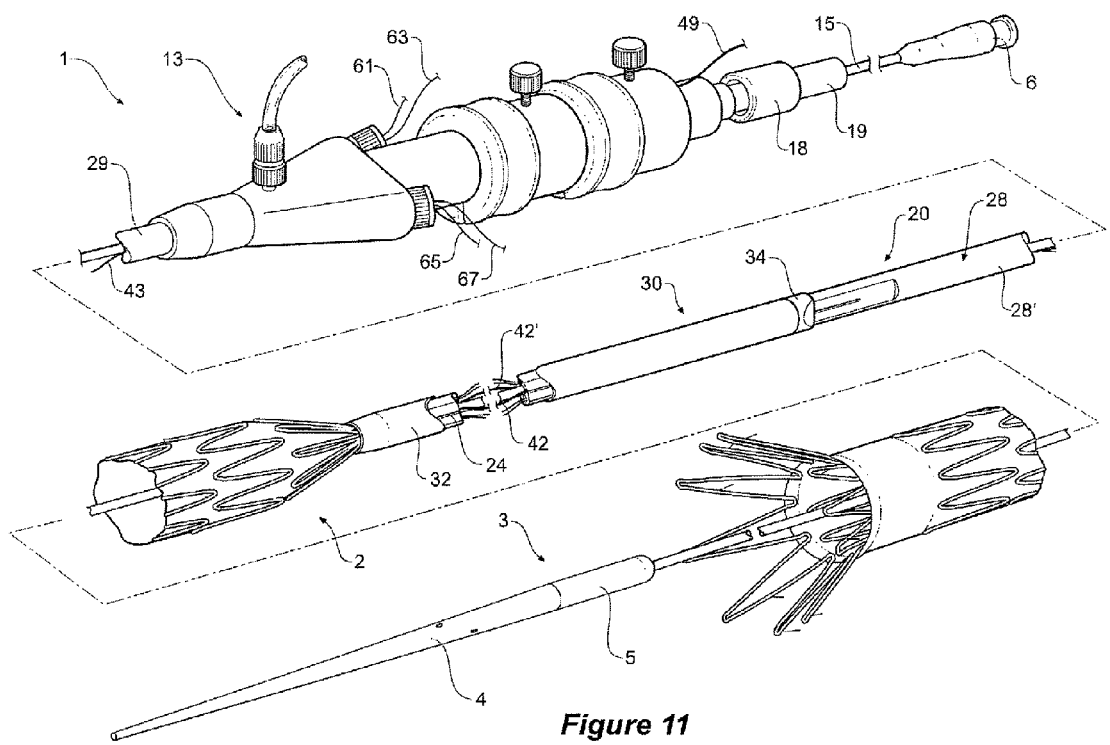
FIG. 11 shows a further embodiment of an endograft and delivery device assembly according to the invention in a diagrammatic isometric view with the endograft covered.
Figure 12:
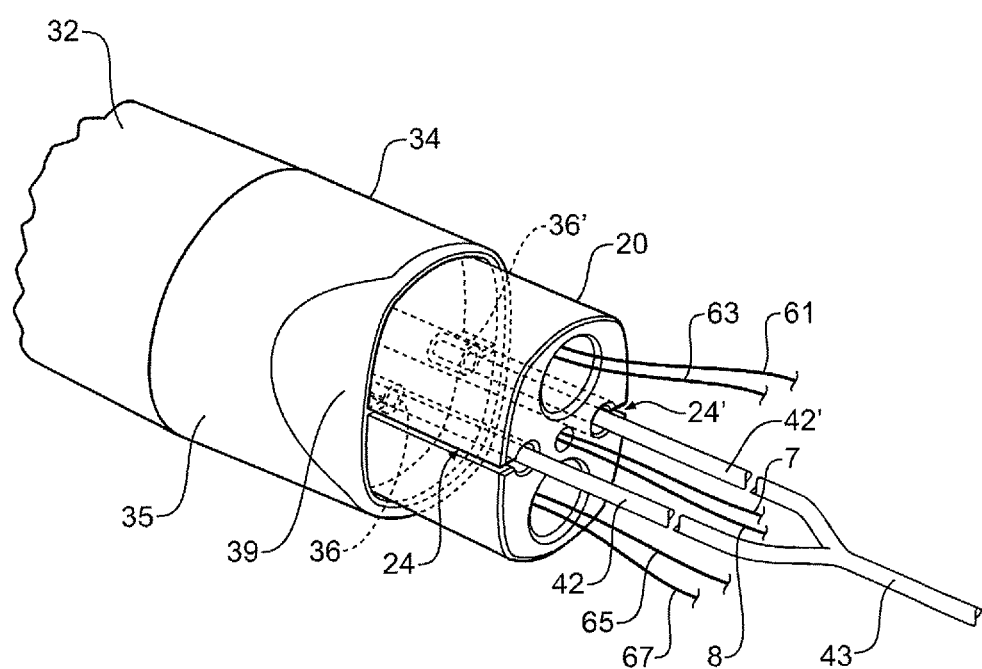
FIG. 12 is a similar figure to FIG. 8A, but also shows auxiliary guide wires.

In some embodiments of the invention, including the embodiment illustrated in FIG. 11, the auxiliary lumens are pre-loaded with respective auxiliary guide wires 61,63 and 65,67. The routing of these auxiliary guide wires through their respective auxiliary lumens is shown most clearly in FIG. 12. The provision of auxiliary lumens 110 and 130 is of assistance where damage to the vasculature includes or is adjacent to one or more branch vessels from a main artery. In such an instance, fenestrated stent grafts may be used and a pusher 20 having auxiliary lumens 110 and 130, as shown on FIG. 5C, facilitates access to the branch vessel or vessels. Thus, with some embodiments of the invention, the pusher 20 may be pre-loaded, as is described in the applicant's earlier applications including International Application No PCT/US2010/020738 titled "PRELOADED STENT GRAFT DELIVERY DEVICE".

Figure 7:
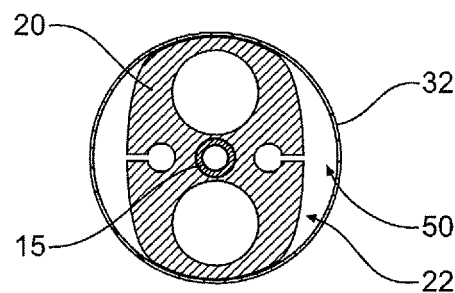
FIG. 7 is a cross-sectional view through plain 91 as indicated on FIG. 1B.

Referring now to FIG. 7, it can be seen that the sheath portion 32 of the sheath assembly 30 is tubular with a circular cross-section. FIG. 7 also shows that the sheath assembly receiving portion 22 of the pusher 20 has a major diameter 21B and a minor diameter 21A, as illustrated in FIG. 5A. The minor diameter 21A is less than the major diameter 21B such that a void 50 is formed between the sheath portion 32 and the pusher 20 when the pusher is in the retracted position, as is illustrated in FIG. 3B. This arrangement reduces the cross-sectional area and reduces the frictional force between the sheath assembly 30 and the pusher 20. It also assists in allowing the overall assembly 1 to flex and follow the tortuous anatomy of the vascular system.

Referring to FIG. 1A, it can be seen that the groove 24 or grooves 24' do not extent into the main portion 28 of the sheath 20 such that the outer surface 28' of the main portion 28 is smoother than the sheath assembly receiving portion 22. This facilitates sealing of the pusher as it passes through an incision 80 in the artery, such as the femoral artery, as illustrated in FIG. 10B.

Referring now to FIG. 6, a cross-sectional view through section lines C-C indicated on FIG. 3A, it can be seen that the outer surface 28' of the main portion is substantially circular in cross-section. This may also assist in minimising leakage through the afore-mentioned incision 80.

Figure 9:
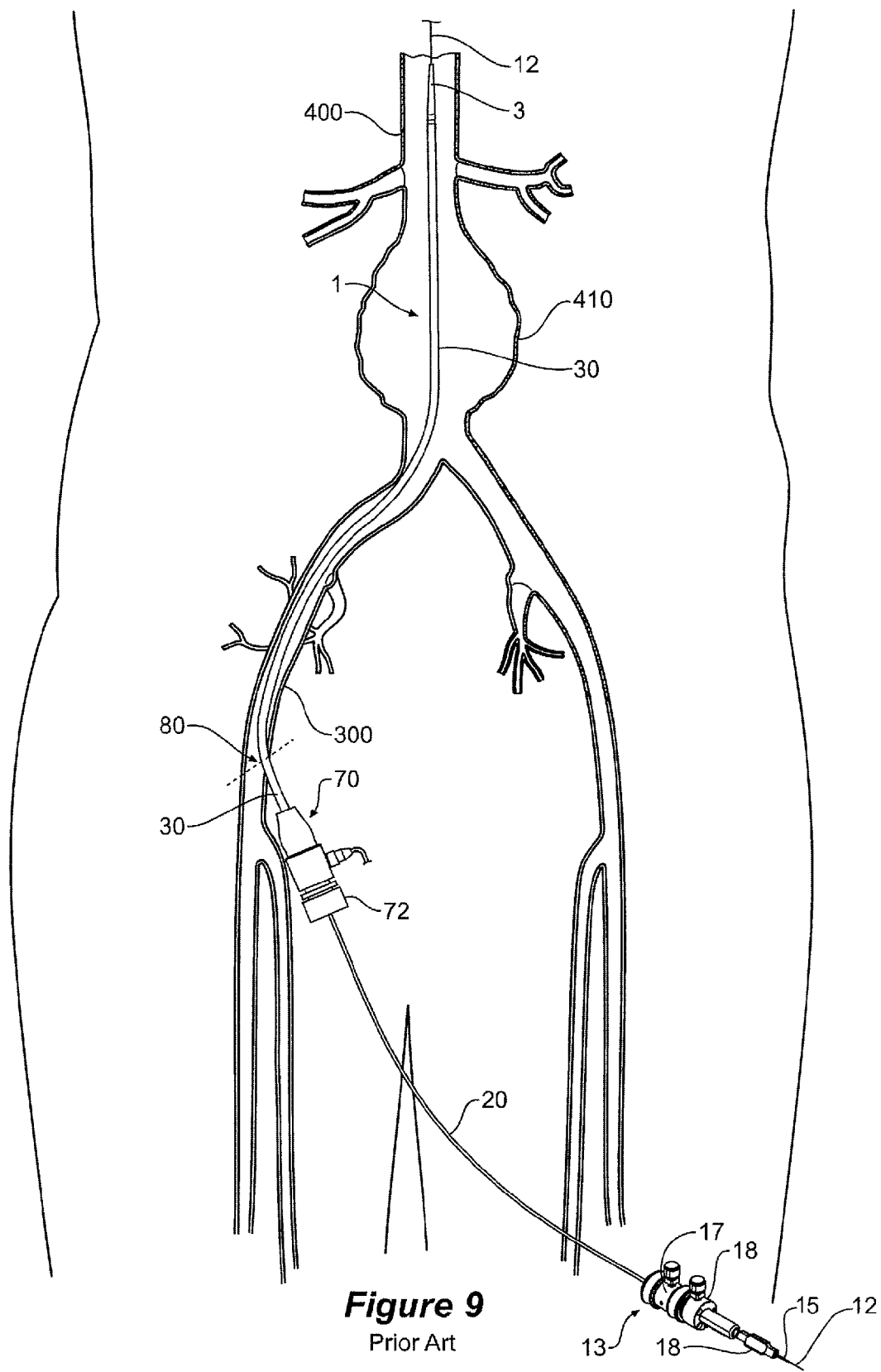
FIG. 9 is a diagrammatic anatomical view showing a prior art endograft and delivery device assembly within the vascular system of a patient.

FIG. 9 is a diagrammatic anatomical view showing a prior art endograft and delivery device assembly 1 within the vascular system of a patient. The prior art device shown, while effective in many situations, has room for improvements. For instance, the ability to prevent blood loss with the endograft delivery device assembly 1 is heavily reliant on a haemostatic valve 70 (such as a Captor® valve) and its valve portion 72. Furthermore, with the prior art arrangement shown in FIG. 9, two portions of the assembly 1 are pushed towards each other so as to cause retraction of the sheath 30 from around the stent graft. While performing the retraction, the surgeon must ensure that there is minimal movement of the pusher in order to avoid movement of the stent graft away from the target location.

Figure 10A:
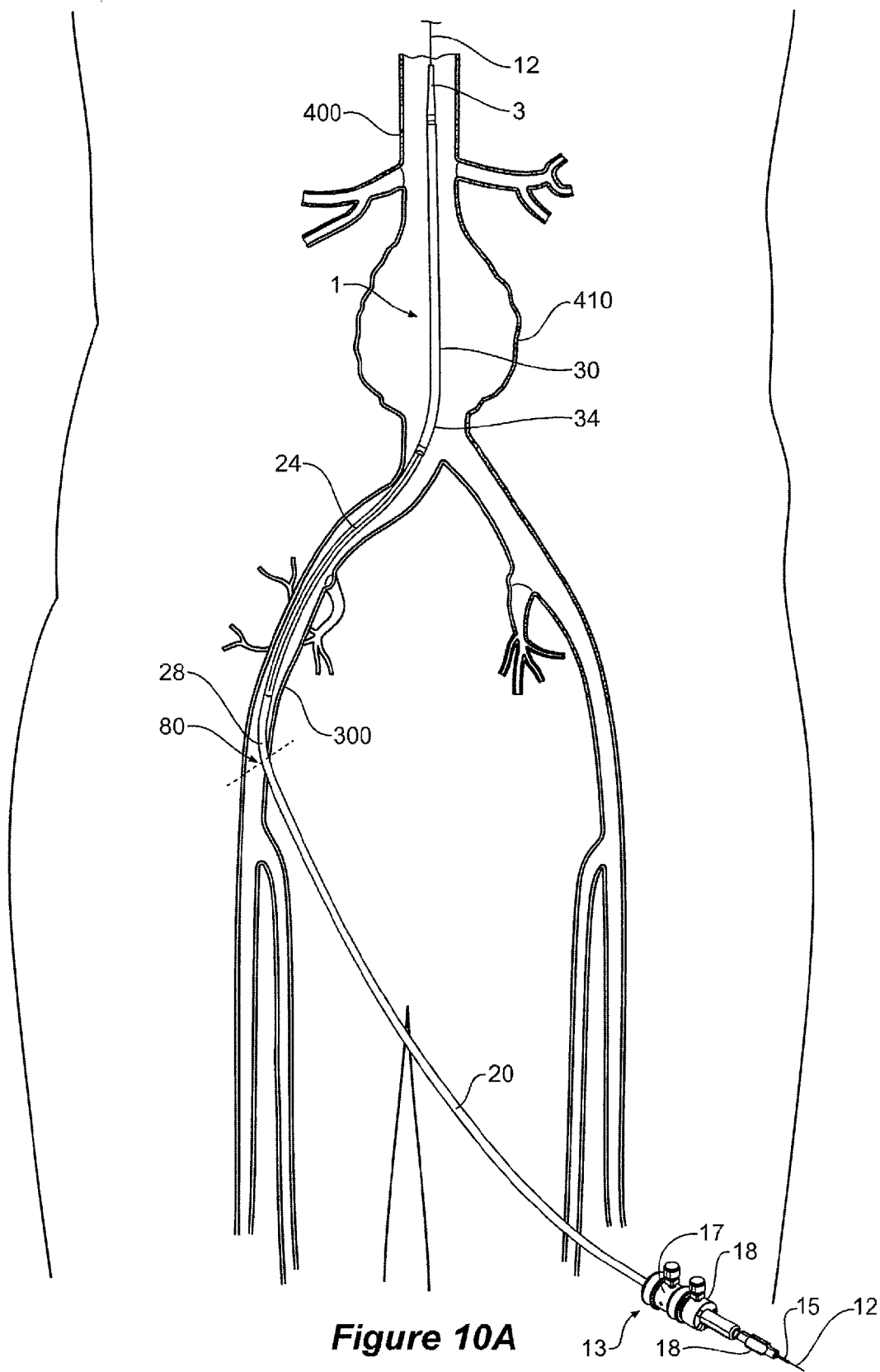
FIG. 10A is a diagrammatic anatomical view according to the invention within the vascular system of a patient, just before deployment.
Figure 10B:
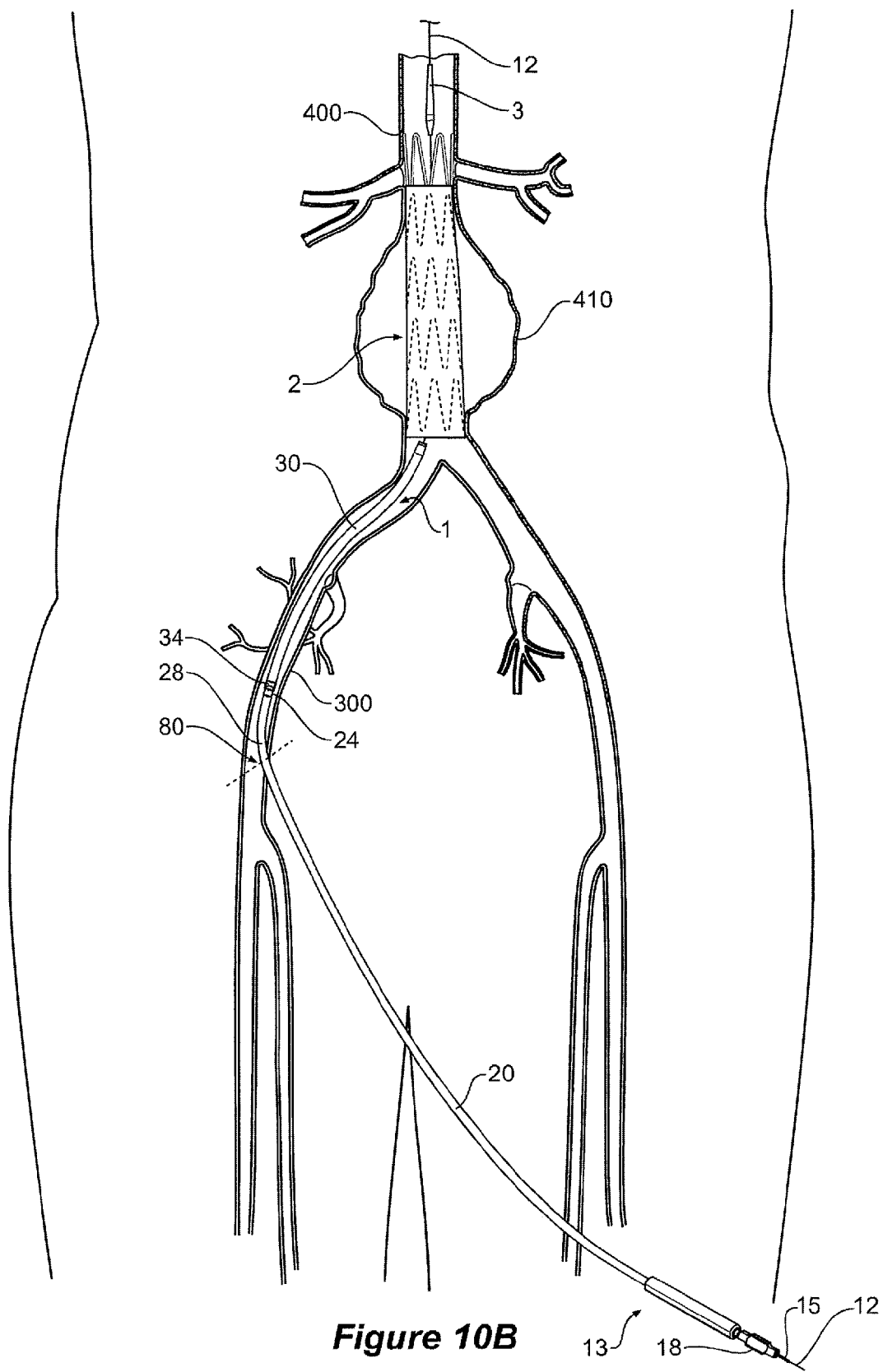
FIG. 10B is a diagrammatic anatomical view according to the invention within the vascular system of a patient, just after deployment.

In contrast to the prior art arrangement shown in FIG. 9, FIG. 10A shows the endograft delivery device assembly 1 of the present invention passing up through and into the femoral artery of a patient and in position to deliver a stent graft to an aneurysmic portion 410 of an aorta 400. No haemostatic valve 70 (or Captor® valve) is required since the outer surface 28' of the pusher 20 itself is sealed against the femoral artery. Minimal movement of the pusher 20, relative to the incision 80 is required since retraction is actuated by the sheath lines 42, 42' and 43 which are wholly inside of the pusher 20 in the region of the incision 80.

FIG. 10B is a similar view to that of FIG. 10A, but shows the sheath assembly 30 retracted and the stent graft 2 deployed. In transitioning from the configuration shown in FIGS. 1A and 10A to the position shown in FIGS. 1B and 10B, the entire sheath assembly 30 is kept entirely within the patient. This eliminates, or at least greatly reduces, movement through the incision 80 and hence assists with minimising blood loss.

An advantage of the embodiments of the invention illustrated and shown in FIGS. 10A and 10B is that, once the device has been inserted up through the femoral artery, there is less likelihood of movement of the stent graft being delivered because the retraction of the short internal sheath 30 is a pull only process. More specifically, the pullable end 49 of the common sheath line 43 can be pulled manually or with a retraction mechanism while the handle 13 is held stationary.

Embodiments of the invention will be significantly shorter in length that current delivery devices. This shorter length makes the assembly easier to use in theatre, reduces shipping costs and facilitates sterilisation (many sterilisation chambers are not large enough to accommodate delivery systems required by taller patients with aneurysms high in the anatomy).

A further advantage of the embodiments of the invention is that the sheath is locked into two parallel grooves 24, 24' within the sheath assembly portion 22 of the pusher 20 and cannot twist or rotate with respect to the pusher.

Embodiments of the invention will be used by vascular surgeons to treat aneurysms and to repair regions of the aorta, including the aortic arch, the thoracic aorta, the abdominal aorta and the aortic bifurcation. Alternative embodiments of the invention will be used in other parts of the vasculature system.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

What is claimed is:

1. An endograft delivery device assembly, the assembly comprising:
    a tip;
    a guide wire cannula, the guide wire cannula extending distally from the tip to a handle at a distal end of the delivery device assembly, the guide wire cannula slidable over a guide wire;
    a pusher disposed around the guide wire cannula, the pusher having a sheath assembly receiving portion at a proximal end thereof and a main portion extending distally from the sheath assembly receiving portion to a distal end, the sheath assembly receiving portion having at least one longitudinally extending groove; and
    a sheath assembly slidably mounted to the sheath assembly receiving portion of the pusher, the sheath assembly having a sheath portion, mountable over a endograft, and slide connecter portion, the slide connector portion having at least one entirely inwardly projecting key, the at least one entirely inwardly projecting key keying with the at least one longitudinally extending groove,
    wherein the sheath assembly, including the sheath portion, the slide connector portion and the at least one entirely inwardly projecting key, is configured to be introduced into a vessel of the patient,
    wherein the sheath assembly is slidably movable from an extended position over the endograft to a retracted position in which the endograft is uncovered;
    a sheath retraction assembly extending longitudinally through the pusher, the sheath retraction assembly connected to the at least one inwardly projecting key and actuatable so as to pull the sheath assembly from the extended position to the retracted position,
    wherein the sheath retraction assembly comprises at least one sheath line, the at least one sheath line directly connected to the at least one inwardly projecting key.

2. The assembly as claimed in claim 1 wherein the at least one longitudinally extending groove in the pusher comprises a pair of longitudinally extending grooves and the at least one inwardly projecting key of the slide connector portion comprises a pair of inwardly projecting keys, wherein one key of the pair of inwardly projecting keys is keyed with one of the pair of longitudinally extending grooves and the other of the pair of inwardly projecting keys is keyed with the other of the pair of longitudinally extending grooves.

3. The assembly as claimed in claim 2 wherein each groove of the pair of longitudinally extending grooves comprises a slot opening into a line receiving passage.

4. The assembly as claimed in claim 3 wherein the at least one sheath line comprises a pair of sheath lines and the slots are mutually sized such that the pair of sheath lines are captive within a respective one of the line receiving passages.

5. The assembly as claimed in claim 2 wherein the sheath retraction assembly comprises a pair of sheath lines, each sheath line connected to a respective key of the pair of inwardly projecting keys.

6. The assembly as claimed in claim 5 wherein the pair of sheath lines are joined at a position distal of the keys and wherein a common sheath line extends distally to a pullable end, the pullable end adjacent to the handle.

7. The assembly of claim 6 wherein the outer surface of the main portion is substantially circular in cross-section.

8. The assembly of claim 1 wherein the sheath portion is tubular with a circular cross-section and wherein the sheath assembly receiving portion of the pusher has a major diameter and a minor diameter, the minor diameter less that the major diameter such that a void is formed between the sheath portion and the pusher when the pusher is in the retracted position.

9. The assembly of claim 1 wherein the at least one longitudinally extending groove does not extend into the main portion of the pusher such that an outer surface of the main portion is smoother than the sheath assembly receiving portion.

10. The assembly of claim 1 wherein the pusher comprises a guide wire cannula receiving lumen and a pair of auxiliary lumens wherein one of the auxiliary lumens is disposed on one side of the guide wire cannula receiving lumen and the other of the auxiliary lumens is disposed on the other side of the guide wire cannula receiving lumen.

11. The assembly of claim 10 wherein the auxiliary lumens are pre-loaded with respective auxiliary guide wires.

12. The assembly of claim 10 wherein the endograft is a stent graft.

13. The assembly of claim 10 wherein the slide connecter portion transitions from a circular end to a non-circular end, the non-circular end shaped to follow an external shape of the sheath assembly receiving portion of the pusher.

14. The assembly as claimed in claim 1 comprising an endograft disposed between the guide wire cannula and the sheath portion of the sheath assembly.

15. The assembly as claimed in claim 14 where the endograft is a stent graft.

16. An endograft and delivery device assembly, the assembly comprising:
    a tip including a dilator portion;

a guide wire cannula, the guide wire cannula extending distally from the tip to a handle at a distal end of the delivery device assembly, the guide wire cannula slidable over a guide wire;

a pusher disposed around the guide wire cannula, the pusher having a sheath assembly receiving portion at a proximal end thereof and a main portion extending distally from the sheath assembly receiving portion to a distal end, the sheath assembly receiving portion having a pair of longitudinally extending grooves, each groove comprising a slot opening into a line receiving passage;

a sheath assembly slidably mounted to the sheath assembly receiving portion of the pusher, the sheath assembly having a sheath portion, mountable over a endograft, and slide connecter portion, the slide connector portion having a pair of entirely inwardly projecting keys, the keys keying with the grooves; and a sheath retraction assembly extending longitudinally through the pusher, the sheath retraction assembly comprising a pair of sheath lines, each sheath line directly connected to a respective key, wherein the sheath retraction assembly is actuatable so as to pull the sheath assemble from an extended position over the endograft to a retracted position in which the endograft is uncovered, and wherein the sheath assembly, including the sheath portion, the slide connector portion and the at least one entirely inwardly projecting key, is configured to be introduced into a vessel of the patient.

17. The assembly as claimed in claim 16 comprising a stent graft disposed between the guide wire cannula and the sheath portion of the sheath assembly.

* * * * *